(12) United States Patent
Sekiguchi et al.

(10) Patent No.: US 9,197,156 B2
(45) Date of Patent: Nov. 24, 2015

(54) OSCILLATION ELEMENT, OSCILLATOR, AND IMAGING APPARATUS USING THE SAME

(71) Applicant: CANON KABUSHIKI KAISHA, Tokyo (JP)

(72) Inventors: Ryota Sekiguchi, Kawasaki (JP); Masahiro Okuda, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 43 days.

(21) Appl. No.: 13/745,546

(22) Filed: Jan. 18, 2013

(65) Prior Publication Data
US 2013/0187721 A1 Jul. 25, 2013

(30) Foreign Application Priority Data

Jan. 19, 2012 (JP) .................................. 2012-009336
Jan. 17, 2013 (JP) .................................. 2013-006315

(51) Int. Cl.
| H03B 7/14 | (2006.01) |
| H03B 5/18 | (2006.01) |
| H01Q 1/38 | (2006.01) |
| H03B 7/08 | (2006.01) |
| G01N 21/3581 | (2014.01) |
| H01Q 11/08 | (2006.01) |

(52) U.S. Cl.
CPC .............. *H03B 5/18* (2013.01); *G01N 21/3581* (2013.01); *H01Q 1/38* (2013.01); *H03B 7/08* (2013.01); *H03B 7/14* (2013.01); *H01Q 11/08* (2013.01)

(58) Field of Classification Search
CPC ............ G06K 19/0723; G06K 7/0008; G06K 19/0701; G06K 19/0715; G06K 7/10178; G06K 17/00; G06K 19/0675; G06K 2017/0051; G06K 19/0707; G06K 19/0712; G06K 19/0724; H02J 17/00; H02J 5/005; H02J 7/025; H04B 5/0031; H04B 5/0037; H04B 5/02; H04B 1/036; H04B 7/022; H04B 7/0421; H04B 7/043; H04B 7/0443; H04B 7/0669; H04B 7/0689; H04B 1/40; H04B 17/0047; H04B 17/0077; H04B 1/1027; H04B 1/408; H04B 5/0068; H03B 7/08; H01Q 1/36; H01Q 1/38; H01Q 3/2617; H01Q 3/2605
USPC ..... 343/721, 701, 700 MS, 843; 331/107 SL, 331/107 T, 52, 55, 96; 333/250
See application file for complete search history.

(56) References Cited

U.S. PATENT DOCUMENTS

| 5,084,706 | A * | 1/1992 | Ross et al. ..................... 342/368 |
| 6,049,308 | A * | 4/2000 | Hietala et al. ........... 343/700 MS |
| 7,583,074 | B1 * | 9/2009 | Lynch et al. ................... 324/120 |
| 2013/0188041 | A1 * | 7/2013 | Sekiguchi et al. ............ 348/135 |

* cited by examiner

*Primary Examiner* — Arnold Kinkead
(74) *Attorney, Agent, or Firm* — Canon U.S.A., Inc. IP Division

(57) ABSTRACT

An oscillation element includes an antenna for oscillation configured to oscillate electromagnetic waves, and multiple negative resistance elements electrically connected to the antenna in parallel, and the multiple negative resistance elements are disposed in only a place where the phases of electromagnetic waves oscillated therefrom are the common phase or opposite phase.

25 Claims, 14 Drawing Sheets

$\phi = 0, \varepsilon = 0$ $\phi = \pi/16, \varepsilon = 0.4$ $\phi = 0, \varepsilon = 0.1$ $\phi = \pi/8, \varepsilon = 0.4$ $\phi = 0, \varepsilon = 0.4$ $\phi = \pi/4, \varepsilon = 0.4$ $|\phi| = \pi/16$, $\varepsilon = 0.4$ $|\phi| = \pi/8$, $\varepsilon = 0.4$ $|\phi| = \pi/4$, $\varepsilon = 0.4$ $\phi xy = 7\pi/8$, $\phi yz = 9\pi/8$, $\varepsilon = 0.4$ $\phi xy = 9\pi/8$, $\phi yz = 7\pi/8$, $\varepsilon = 0.4$

CASE OF DIPOLE ANTENNA

CASE OF SLOT ANTENNA

CASE OF PATCH ANTENNA

OSCILLATION ELEMENT, OSCILLATOR, AND IMAGING APPARATUS USING THE SAME

BACKGROUND OF THE INVENTION

1. Field of the Invention

The present invention relates to an oscillation element or oscillator configured to oscillate electromagnetic waves, and an imaging apparatus using the same.

2. Description of the Related Art

Heretofore, a configuration having an antenna (resonator) and a negative resistance element such as a resonant tunneling diode or the like is effective as an electromagnetic-wave oscillation element. There have been known an oscillation element or oscillator using a negative resistance element such as a resonant tunneling diode or the like and an antenna to generate electromagnetic waves including at least a part of frequency components of frequency bands from millimeter bands (30 GHz to 300 GHz) to terahertz bands (300 GHz to 30 THz).

Oscillation output of such an oscillation element tends to decrease along with increase in the oscillation frequency of electromagnetic waves to be oscillated. For example, though output as much as a mW class is obtained at around 100 GHz, output deteriorates to a μW class at around 1 THz. One cause for deterioration in oscillation output is miniaturization of a junction area of negative resistance elements along with increase in an oscillation frequency.

In general, it has been known that a negative resistance element such as a resonant tunneling diode or the like forms a RC low-pass filter function made up of a junction capacitor Cj and a serial resistor Rs equivalent to resistance from the negative resistance element to a resonator. Specifically, a high-frequency component of a signal is shielded by the RC low-pass filter function, and oscillating of electromagnetic waves in a higher frequency band than a cutoff frequency fc ($=(2\pi \times RsCj)^{-1}$) is not readily realized. Therefore, a cutoff frequency serving as the upper limit of a frequency band to be oscillated by an oscillation element has to be higher than the frequency band of electromagnetic waves to be oscillated. Here, the junction capacitor Cj is proportional to the junction area of a negative resistance element, and accordingly, the junction area has to be reduced as one method to increase the cutoff frequency fc ($=(2\pi \times RsCj)^{-1}$). On the other hand, the power of a power source which can be supplied to the negative resistance element is also proportional to the junction area of the negative resistance element. Accordingly, power which can be supplied to the negative resistance element is also decreased along with increase in an oscillation frequency, and oscillation output is also deteriorated.

Therefore, with U.S. Pat. No. 6,049,308 specification, in order to suppress deterioration in oscillation output, there has been disclosed a configuration of an oscillation element including multiple resonant tunneling diodes at a patch antenna resonator.

However, with U.S. Pat. No. 6,049,308 specification, multiple negative resistance elements are arrayed in a straight line, and accordingly, electromagnetic waves which all of the negative resistance elements oscillate have not been synchronized. Specifically, the multiple resistance elements are disposed with the common interval in the center portion of the antenna (resonator), and accordingly, there are negative resistance elements which mutually differ in the frequencies and phases of electromagnetic waves to be resonated and oscillated, and accordingly, the negative resistance elements have oscillated in a state in which electromagnetic waves having a different frequency and phase are mixed, which has in turn caused deterioration in oscillation output of the oscillation element.

SUMMARY OF THE INVENTION

Accordingly, it has been found to be desirable to provide an oscillation element of which oscillation output has been improved by all of negative resistance elements disposed in an antenna being synchronized to oscillate electromagnetic waves having the common frequency and common phase.

An oscillation element provided by an embodiment of the present invention is an oscillation element configured to oscillate electromagnetic waves, and includes: an antenna configured to guide electromagnetic waves; and multiple negative resistance elements electrically serially connected to the antenna, and also connected to each other in parallel, and the multiple negative resistance elements are disposed in a position alone where the phases of electromagnetic waves which the corresponding negative resistance elements oscillate mutually are the same phase in a substantial manner or become the opposite phase in a substantial manner.

The present invention encompasses an oscillator and an imaging apparatus.

An oscillator according to an embodiment of the present invention is an oscillator configured to oscillate electromagnetic waves, and includes: the oscillation element according to an embodiment of the present invention; and a power source unit configured to apply DC voltage to the oscillation element.

An imaging apparatus according to an embodiment of the present invention is an imaging apparatus configured to image an object to be measured using electromagnetic waves, and includes: the oscillator according to an embodiment of the present invention configured to oscillate electromagnetic waves to an object to be measured; a detector configured to detect electromagnetic waves transmitted through or reflected at the object to be measured; and an image forming unit configured to form an image regarding the object to be measured from information relating to electromagnetic waves detected by the detector.

According to the present invention, there may be provided an oscillation element of which the oscillation output to oscillate electromagnetic waves has been improved.

Further features of the present invention will become apparent from the following description of exemplary embodiments with reference to the attached drawings.

DESCRIPTION OF THE EMBODIMENTS

Figure 1A:
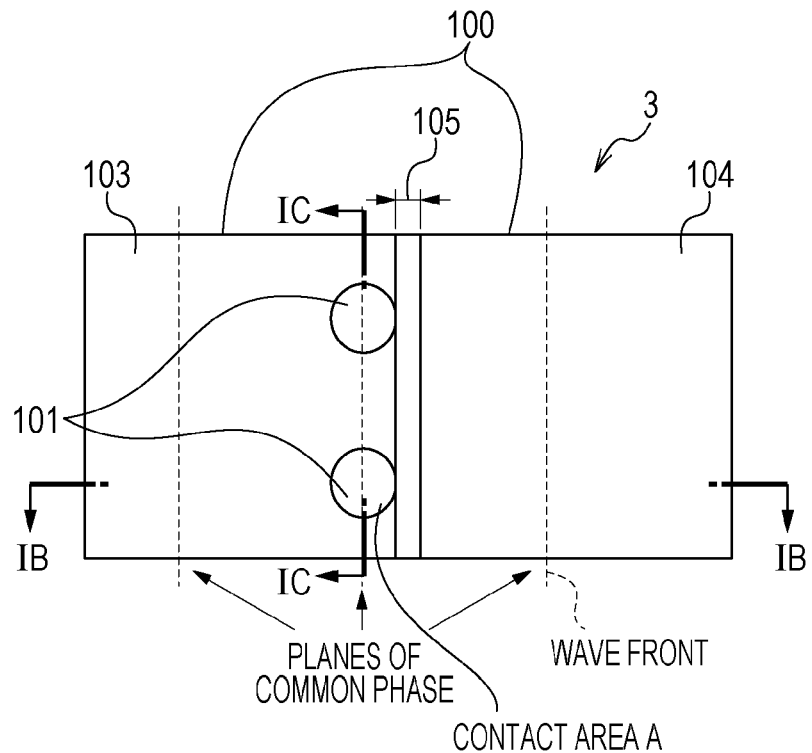
FIG. 1A is a diagram illustrating a schematic configuration of an oscillation element according to a first embodiment.

An oscillation element according to an embodiment of the present invention has a configuration to improve oscillation output of the oscillation element. The oscillation element according to an embodiment of the present invention includes a single or multiple antennas which guide electromagnetic waves, and multiple negative resistance elements electrically serially connected to the antennas and also mutually connected in parallel.

Also, with the oscillation element according to an embodiment of the present invention, the multiple negative resistance elements are disposed only in a position where the phases of electromagnetic waves which the corresponding negative resistance elements oscillate mutually are the same phase in a substantial manner, or a position where the phases of electromagnetic waves which the corresponding negative resistance elements oscillate mutually become the opposite phase in a substantial manner.

The position where the phases of electromagnetic waves which the corresponding negative resistance elements oscillate mutually are the same phase in a substantial manner, or the position where the phases of electromagnetic waves which the corresponding negative resistance elements oscillate mutually become the opposite phase in a substantial manner may be regarded as a position where the oscillation frequencies which the corresponding negative resistance elements oscillate become equal.

According to the oscillation element according to an embodiment of the present invention, all of the negative resistance elements to be disposed in the antenna are allowed to oscillate electromagnetic waves by combining and synchronizing electromagnetic waves of one oscillation frequency, and accordingly, the oscillation output of the oscillation element may be improved.

Note that, with the present invention, disposing the multiple negative resistance elements only in a position where the phases of electromagnetic waves which the corresponding negative resistance elements oscillate mutually are the same phase in a substantial manner, or a position where the phases of electromagnetic waves which the corresponding negative resistance elements oscillate mutually become the opposite phase in a substantial manner, encompasses the following.

Specifically, according to each of the multiple negative resistance elements, displacement is not restricted to displacement where phase difference of electromagnetic waves to be oscillated and propagated becomes 0 or $\pi$, and is allowed to be extended to displacement including a predetermined range. With the oscillation element according to the present embodiment, a case where the absolute value of phase difference for each electromagnetic wave to be oscillated and propagated is 0 or greater and $\pi/8$ or less, is also included in the common phase. Displacement for the negative resistance elements will be described later in detail.

Here, examples of negative resistance elements 101 may include a negative resistance element such as a resonant tunneling diode (RTD), a resonant interband tunneling diode (RITD), a Gunn diode, an IMPATT diode, a TUNNET diode, or the like. Alternatively, a base-emitter configuration at a transistor, or a gate-source configuration at an FET (Field-effect transistor) may be substituted for a negative resistance element.

On the other hand, examples of the antenna may include a dipole antenna, a slot antenna, a patch antenna, a Cassegrain antenna, a parabolic antenna, or the like. Also, the antenna is not restricted to a planar antenna, and may be a stereo antenna.

Hereinafter, embodiments of the present invention will be described in detail based on the drawings. Note that, for ease of description, with the first through third embodiments, the concepts of the present invention will be described, and specific configurations will be described in the subsequent embodiments.

First Embodiment

Configuration of Resonance Element

Figure 1B:
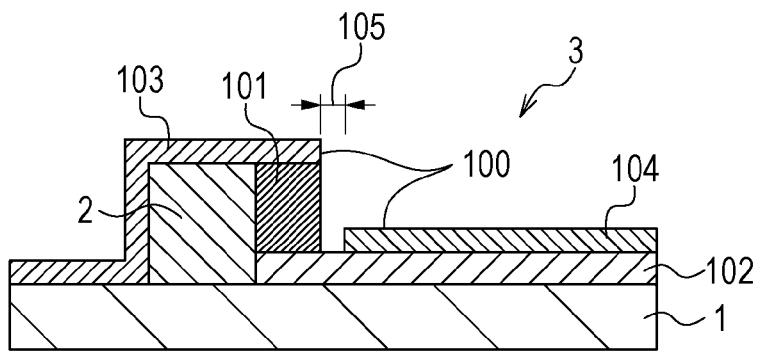
FIG. 1B is a diagram illustrating a portion of a cross section perpendicular to planes of the common phase of electromagnetic waves of the oscillation element according to the first embodiment.
Figure 1C:
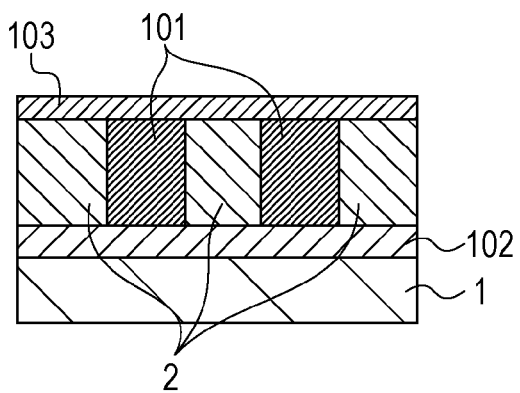
FIG. 1C is a diagram illustrating a cross section parallel to the planes of the common phase of electromagnetic waves of the oscillation element according to the first embodiment.

FIG. 1A is a schematic diagram illustrating a portion of the resonance element according to the present embodiment. FIG. 1B is a diagram illustrating a portion of a cross section perpendicular to planes of the common phase of electromagnetic waves of the oscillation element according to the present embodiment. FIG. 1C is a diagram illustrating a cross section parallel to planes of the common phase of electromagnetic waves of the resonance element according to the present embodiment.

An oscillation element 3 according to the present embodiment is an element which enables to oscillate electromagnetic waves (hereinafter, referred to as terahertz waves) including a portion of frequency bands from a millimeter band to a terahertz band, i.e., between 30 GHz and 30 THz.

As illustrated in the drawings, the oscillation element 3 includes two negative resistance elements 101, strip conductors 103 and 104 which are antennas for oscillation which guide electromagnetic waves. The two negative resistance elements 101 are electrically connected to the strip conductors 103 and 104 which guide electromagnetic waves, respectively. Here, the antennas are made up of a pair of conductors, and the multiple negative resistance elements are apposed in contact with one conductor of this pair. Also, the oscillation element 3 includes a substrate 1 and a dielectric 2.

As illustrated in FIG. 1A, the oscillation element 3 according to the present embodiment includes two negative resistance elements 101 which are electrically connected in parallel, and the negative resistance elements 101 are disposed so as to have the same phase as the electromagnetic waves to be oscillated.

The negative resistance elements 101 have to have a fine junction area so as to oscillate electromagnetic waves including a portion of frequency bands from a millimeter band to a terahertz band, i.e., from 30 GHz to 30 THz. The junction areas of the negative resistance elements mentioned here are areas which provide negative resistance to current-voltage properties. Each of the areas may be regarded as the area of a cross section perpendicular to a direction where the current of the junction portion (semiconductor active layer) which makes up a negative resistance element.

Dimensions thereof are 1 $\mu m^2$ or less in the event of employing silicon as a material which makes up the negative resistance elements 101. Also, of compound semiconductor materials having relatively high mobility, the dimensions are 10 $\mu m^2$ or less in the event of a Group III-V semiconductor material such as GaAs or the like.

Therefore, with the present embodiment, the junction area of a negative resistance element which is in contact with the antenna may be set to 10 $\mu m^2$ or less. This is because typical junction thickness at a resonant tunnel diode which is one of negative resistance elements is several tens of nano-millimeters, and the relative permittivity is around 10, and accordingly, the junction capacitor Cj is determined in proportional to the junction area.

Also, though this depends on the mobility of the semiconductor material it is difficult to decrease series resistance from a negative resistance element to an oscillator, such as metal or the like, to 100Ω or lower. Therefore, the negative resistance elements have to have the above-mentioned junction area, and accordingly, the cutoff frequency fc ($=(2\pi \times RsCj)^{-1}$) have to be increased.

Also, as illustrated in FIGS. 1B and 1C, the two negative resistance elements 101 are each in contact with the strip conductor 103. Also, the negative resistance elements 101 are also in contact with a semiconductor area 102. The shapes of the negative resistance elements 101 according to the present embodiment are uniform cylinders, and the circumferences of the negative resistance elements 101 are surrounded with the dielectric 2. This dielectric 2 is significantly high in resistance for electromagnetic waves to be propagated as compared to the negative resistance elements 101. Also, the negative resistance elements 101 are also in contact with the semiconductor layer 102.

Thus, the two strip conductors 103 and 104 are electrically in ohmic contact with each other via the negative resistance elements 101 and semiconductor layer 102. That is to say, at least one of the conductors which make up the antennas and a negative resistance element are electrically serially connected via the semiconductor layer.

The reason why these are not directly connected without passing through the semiconductor layer 102 is because this is approximate to the precision limit of photolithography, and a gap 105 equivalent to precision limit in manufacturing occurs between the negative resistance elements 101 and the strip conductor 104.

In order to fill this gap 105, the gap 105 is filled by passing through the semiconductor layer 102 which has lower electrical conductivity than that of the strip conductor 104 as appropriate. Thus, the negative resistance elements 101 and strip conductor 104 are electrically in ohmic contact with each other via this semiconductor layer 102.

Also, the semiconductor layer 102 serves as the main factor of a series resistor Rs which is a resistance component of the oscillation element from the oscillation element to the strip conductor. Hereinafter, the junction areas between the negative resistance elements 101 and the strip conductor 103 will be referred to as A, and an equivalent circuit of the oscillation element 3 will be described.

Equivalent Circuit of Oscillation Element

Figure 2:
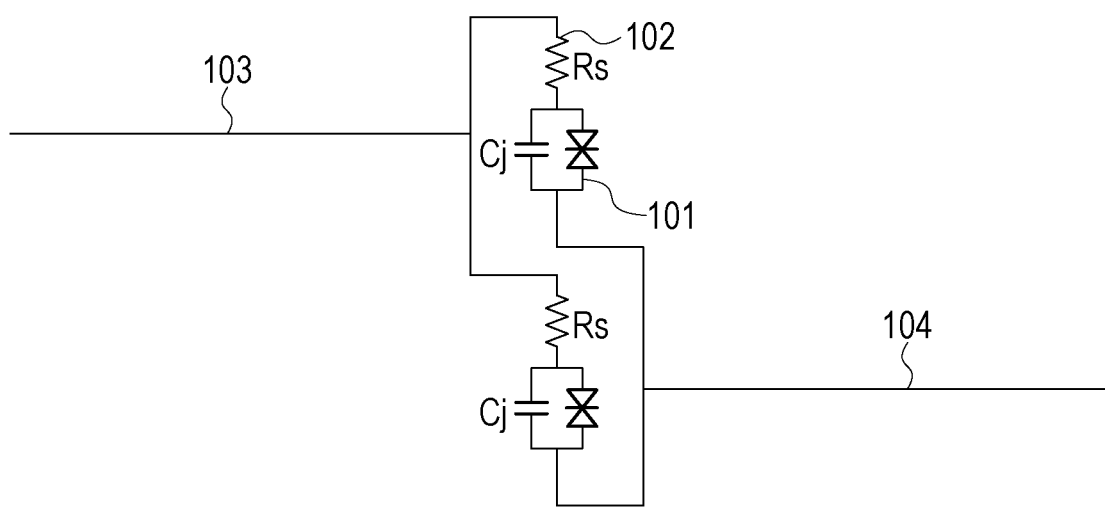
FIG. 2 is a diagram illustrating an equivalent circuit of the oscillation element according to the first embodiment.

FIG. 2 is a diagram illustrating an equivalent circuit of the oscillation element according to the present embodiment. However, here, in order to simplify description, we will say that the equivalent circuit is a circuit made up of only the series resistor Rs which is resistance combined from the negative resistance element 101 and junction capacitor Cj, and the junction capacitor Cj of the negative resistance element. That is to say, the equivalent circuit is regarded as an RC circuit made up of the junction capacitor Cj of the negative resistance element 101, and series resistor Rs, i.e., a low-pass circuit.

Here, the cutoff frequency fc which is a frequency serving as the upper limit of the frequency bands of electromagnetic waves which are allowed to be oscillated at this oscillation element is obtained as fc=$(2\pi \times RsCj)^{-1}$. With the junction area of the negative resistance element 101 as A, the series resistor Rs between the negative resistance element 101 and the strip conductor 104 is inversely proportion to $\sqrt{A}$. On the other hand, the joint capacitor Cj which is regarded as to be held at the negative resistance element 101 is, as described above, ideally proportional to the junction area A of the negative resistance element 101.

The cutoff frequency fc which is a frequency serving as the upper limit of the frequency bands which are allowed to be oscillated at the oscillation element is obtained as fc=$(2\pi \times RsCj)^{-1}$. Here, the series resistor Rs between the resonant tunneling diode 101 and the strip conductor 104 may be regarded as generally the same as the resistor of the semiconductor layer 102, and when a junction area between the Schottky barrier diode 101 and the strip conductor 103 is taken as A, the series resistor Rs between the Schottky barrier diode 101 and the strip conductor 103 is inversely proportion to $\sqrt{A}$. On the other hand, the joint capacitor Cj which is regarded as to be held at the resonant tunneling diode 101 is ideally proportional to the junction area A. That is to say, with regard to the single-handed negative resistance element 101 in a single, relationship of RsCj∝$\sqrt{A}$ holds.

Here, in order to improve oscillation output by decreasing combined resistance of the oscillation element, the resistance value of the series resistor Rs has to be decreased, and one possible method is to increase the junction areas A of the negative semiconductor areas 101.

However, in the event of increasing one junction area A of the negative resistance elements 101 to double for example, the cutoff frequency fc ($=(2\pi \times RsCj)^{-1}$) which is the upper limit of the frequency bands of electromagnetic waves which are allowed to be oscillated at this oscillation element is decreased to $1/\sqrt{2}$. That is to say, there is a problem in that the frequency bands of electromagnetic waves to be allowed to be oscillated, deteriorate.

Therefore, the oscillation element 3 according to the present embodiment have the two negative resistance elements 101 having the mutually independent junction area A, and accordingly, the combined resistance of the oscillation element may be decreased while suppressing deterioration in the frequency bands of electromagnetic waves to be oscillated. That is to say, oscillation output may be improved as compared to heretofore oscillation elements using the one negative resistance element 101. Hereinafter, description will be made further in detail.

The present embodiment includes the two negative resistance elements 101, the series resistors Rs between each of the negative resistance elements 101 and the strip conductor 104 are connected in parallel, and are distributed to each, and accordingly, the combined resistance combined as the entire oscillation element becomes ½ of the series resistor Rs, i.e., Rs/2. Also, the junction area may be regarded as 2A, and accordingly, parallel capacitance combined as the entire element is double of the junction capacitor Cj, i.e., 2Cj.

Accordingly, as for the entire oscillation element according to the present embodiment, the series resistor Rs becomes ½, and the junction capacitor Cj becomes double as compared to a heretofore oscillation element using one negative resistance element according to the related art. Therefore, when applying the oscillation element according to the present embodiment to the expression of the cutoff frequency fc, the expression becomes fc=$(2\pi \times (Rs/2)2Cj)^{-1}$, and the cutoff frequency is not deteriorated as compared to a heretofore oscillation element including one negative resistance element.

On the other hand, oscillation output of the oscillation element is determined according to the product of supply power and conversion efficiency, and with the configuration of the present embodiment wherein the junction area of the negative resistance elements 101 of the oscillation element is regarded as 2A, as compared to a case where the one negative resistance element 101 is included, supply power to the oscillation element becomes double, and ideally, the oscillation output becomes double.

Here, in order to obtain ideal oscillation output without decreasing the conversion efficiency of the oscillation element 3, it is ideal that injection locking which is a phenomenon in which electromagnetic waves with the common frequency and common phase are oscillated is made by the two arrayed negative resistance elements 101 mutually oscillating electromagnetic waves with a near oscillation frequency.

Therefore, the negative resistance elements 101 have to be disposed so that the electromagnetic-wave positions of the negative resistance elements 101 become equal to those of the electromagnetic waves of a predetermined frequency band to be oscillated (resonated) at the oscillation element 3, i.e., so as to become the same phase. With the present embodiment, the electromagnetic waves to be oscillated (resonated) are standing waves by way of the negative resistance element 101 positioned in the center portion which is between the left strip conductor 103 and the right strip conductor 104.

Accordingly, the two negative resistance elements 101 have to be disposed in a position to generate the common phase for electromagnetic waves to be propagated through the strip conductor 103, and as illustrated in FIGS. 1A to 1C, the two negative resistance elements 101 are disposed in a place of the common wave front of electromagnetic waves to be oscillated. Here, the strip conductors 103 and 104 are planar antennas in the oscillation element, and it is desirable that portions of the strip conductors which are in contact with the negative resistance element 101 are flat portions so as to readily define the phase or wave front (e.g., equipotential plane or the like) of electromagnetic waves at the strip conductors 103 and 104.

Thus described above is a configuration wherein oscillation output restricted by the junction area of the negative resistance element in the event that the number of the negative resistance elements is one is improved to double by disposing the two negative resistance elements in a position where electromagnetic waves have the common phase.

FIGS. 3A to 3F are diagrams for describing injection locking of electromagnetic waves. The numerical calculation indicated in this drawing is understood by analyzing a van der pol nonlinear expression. The expression is as follows.

$$x''(\tau) - \tau(1-x^2(\tau))x'(\tau) + x(\tau) = \lambda_{in}\kappa x_{in}'(\tau)$$

x in this expression represents amount in proportional to voltage to be applied to the negative resistance elements 101, and is represented as $x(\tau)$ to understand dependency of time $\tau=\omega_0 t$ normalized with LC frequency $\omega_0=1\sqrt{LC}$. Also, $x''(\tau)$ and $x'(\tau)$ represent second-order derivative and first-order derivative of $x(\tau)$, respectively.

$x_{in}(\tau)$ is amount in proportional to voltage to be applied to the negative resistance elements 101 externally input, for example, by mutual injection locking or the like, and $\kappa$ is a coupling constant indicating strength of interaction to be applied to between the two negative resistance elements 101. The parameter $\lambda$ has a 1/Q dimension, the $\lambda$ is accompanied with a linear component $g_1<0$ of negative differential conductance of the negative resistance element 101, and load G of the planar antennas 103 and 104, and is represented as $\lambda=-(G+g_1)\sqrt{(L/C)}$. $\lambda_{in}$ is equal to 1/Q of the planar antennas 103 and 104, and is represented as $\lambda_{in}=G\sqrt{(L/C)}$. Note that in the event that the right side of the expression is 0, this is a case where there is no input of electromagnetic waves to the negative resistance elements 101.

With the van der pol nonlinear expression, in the event of a typical case, the solution is orbited on a closed orbit called a limit cycle. When the frequency (oscillation frequency) to be orbited is included in 2% of $\omega_0$, the parameter $\lambda$ is set to $0<\lambda \leq 0.57$. When the $\lambda$ is longer than 0.58, the solution is strongly distorted, and is significantly decreased than the oscillation frequency $\omega_0$. Therefore, the $\lambda$ is set as $\lambda=0.57$ in numeric computation. Also, let us say that the Q values of the planar antennas 103 and 104 are 10, and hereinafter, the $\lambda_{in}$ is set as $\lambda_{in}=0.10$. Now, if we consider a case where injection locking may mutually be performed at the two negative resistance elements 101, the expression becomes as follows.

$$x''(\tau) - \lambda(1-x^2(\tau))x'(\tau) + x(\tau) = \lambda_{in}\kappa_{xy}y'(\tau)$$

$$y''(\tau) - \lambda(1-y^2(\tau))y'(\tau) + y(\tau) = \lambda_{in}\kappa_{yx}x'(\tau)$$

However, the coupling constant that indicates strength of interaction to be applied between the negative resistance elements is taken as $\kappa_{yx}=\kappa_{xy}=\in\exp(i\phi)$ from a reciprocal property. $\in$ is a coupling constant of the two adjacent negative resistance elements 101, and $\phi$ represents phase difference between the two adjacent negative resistance elements 101.

Figure 3A:
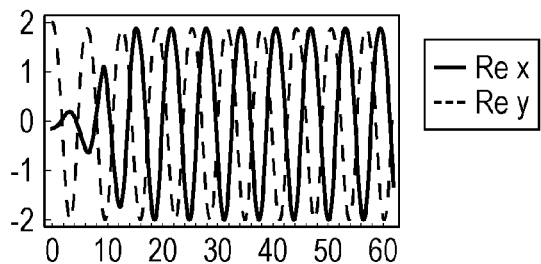
FIGS. 3A to 3F are diagrams illustrating time waveforms of terahertz waves of two negative resistance elements according to the first embodiment.

The drawings are results of numeric computation wherein real components (vertical axis) of x and y are developed until the $\tau$ becomes 10 cycles worth (horizontal axis) with the $\in$ and $\phi$ as parameters. FIGS. 3A, 3B, and 3C represent $\in$ dependency at the time of $\phi=0$, and represent results at the time of setting to $\in=0.0$, $\in=0.1$, and $\in=0.4$ in order of FIGS. 3A, 3B, and 3C. According to these drawings, it turns out that as the coupling constant represented with the $\in$ increases such as $\varepsilon=0.0$, $\varepsilon=0.1$, and $\varepsilon=0.4$, electromagnetic waves which the two negative resistance elements 101 oscillate gradually come closer to each other so as to overlap at the common phase, and finally, synchronization is readily performed. In the event of $\varepsilon=0.4$, the phase difference $\phi$ between the two negative resistance elements 101 is 0, i.e., in the event of the common phase, electromagnetic waves to be oscillated are synchronized.

Now, with the present embodiment, the two negative resistance elements 101 are disposed in the same strip conductors 103 and 104 within the same antenna resonator, and accordingly, $\varepsilon \geq 0.4$ may be expected. Accordingly, since $\varepsilon \geq 0.4$, it turns out that, in the event that the phase difference $\phi$ between the two negative resistance elements 101 is disposed in a position of $\phi=0$, electromagnetic waves which the negative resistance elements 101 oscillate are mutually synchronized in injection.

Figure 3D:
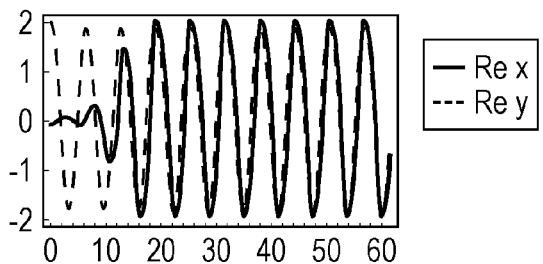
Figure 3B:
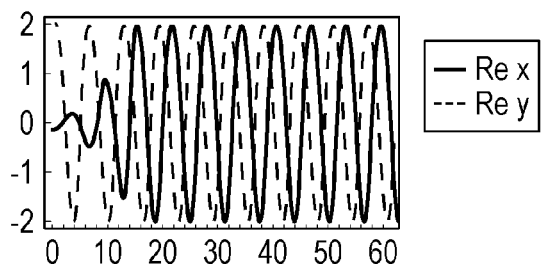
Figure 3E:
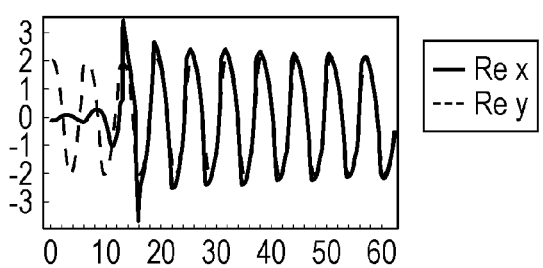
Figure 3C:
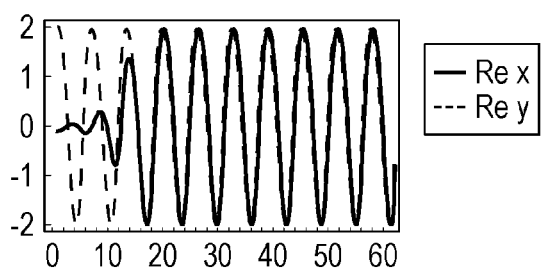
Figure 3F:
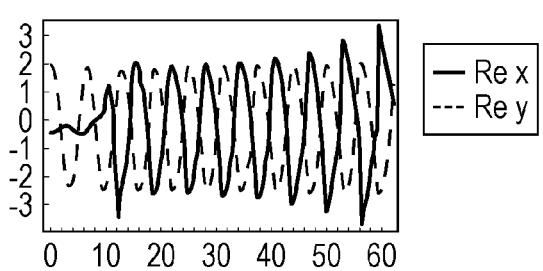

FIGS. 3D, 3E, and 3F are results that indicate $\phi$ dependency of electromagnetic waves at the time of $\varepsilon=0.4$. In order of FIGS. 3D, 3E, and 3F, the phase difference $\phi$ between the two negative resistance elements 101 was set to $\phi=\pi/16$, $\phi=\pi/8$, and $\phi=\pi/4$.

As illustrated in the drawings, in the event of $\varepsilon=0.4$, electromagnetic waves which the negative resistance elements 101 oscillate are mutually synchronized until $\phi=\pi/8$. Accordingly, the positions of the two negative resistance elements 101 do not strictly have to be the position of the phase difference $\phi=0$, and may be extended to a position including phase difference of a predetermined range. According to the oscillation element in FIGS. 3A to 3F, let us say that there may also be included in the common phase a case where the absolute value of the phase difference $\phi$ against electromagnetic waves to be each propagated is between 0 and $\pi/8$. That is to say, according to the oscillation element according the present embodiment, it is desirable as "a position to generate the common phase" to dispose the two negative resistance elements 100 so that the phase difference $\phi$ of the two negative resistance elements 101 is 0 or greater and $\pi/8$ or less. Also, it is more desirable to dispose the two negative resistance elements 100 so that the phase difference $\phi$ of the two negative resistance elements 101 is 0 or greater and $\pi/16$ or less.

Note that, even when inductance components in the two negative resistance elements 101 differ, i.e., even when the RC frequencies $\omega_0=1\sqrt{RC}$ slightly differ, this may be ignored as long as the phase difference $\phi$ is in the common phase. Specifically, even when the RC frequencies $\omega_0$ of the two negative resistance elements differ, mutual injection locking of electromagnetic waves is performed as long as the phase difference $\phi$ of the two negative resistance elements 101 is 0 or greater and $\pi/8$ or less (when expressing this in wavelength, $\lambda_0/16$, i.e., up to around $\pm 3\%$).

Second Embodiment

While the number of the negative resistance elements illustrated in the first embodiment is two, the present embodiment is an embodiment wherein n ($n \geq 3$) negative resistance elements such as resonant tunneling diodes or the like are apposed. The other configurations are the same as with the first embodiment, and accordingly, description regarding these same configurations will be omitted. Hereinafter, an oscillation element according to the present embodiment will be described.

Note that, while the present embodiment is an embodiment wherein n negative resistance elements are apposed in an antenna, an example will be described wherein three negative resistance elements are apposed.

Figure 4A:
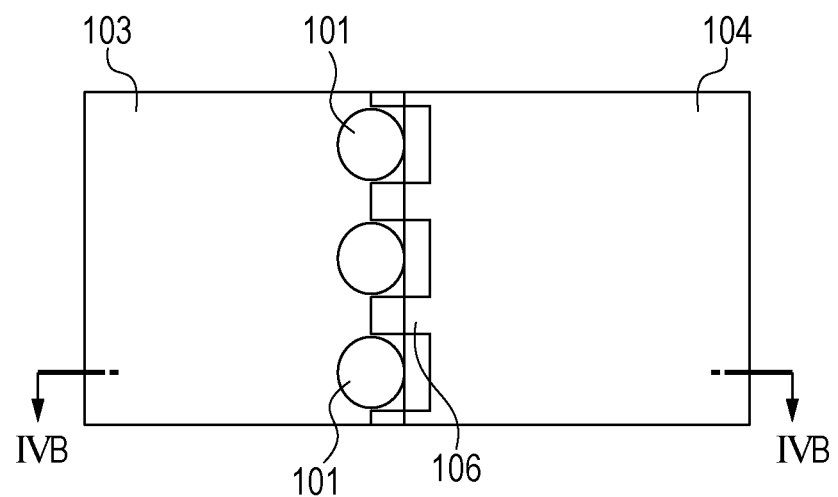
FIG. 4A is a diagram illustrating a schematic configuration of an oscillation element according to a second embodiment.
Figure 4B:
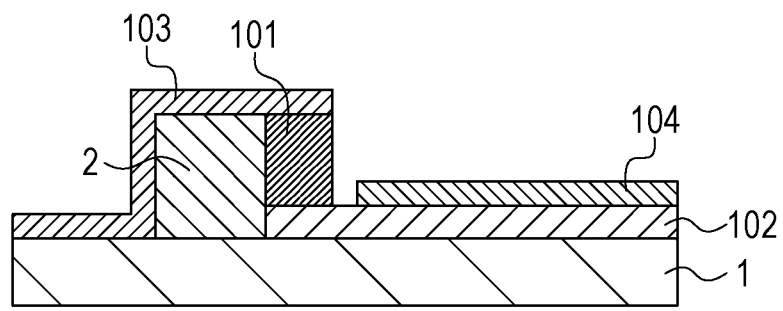
FIG. 4B is a diagram illustrating a cross section of the oscillation element according to the second embodiment.

FIG. 4A is a schematic diagram illustrating a portion of the oscillation element according to the present embodiment. FIG. 4B is a cross-sectional view illustrating a portion of the oscillation element according to the present embodiment.

As with the present embodiment, when apposing the three negative resistance elements 101 in an antenna, parallelization efficiency of the series resistor Rs has to be taken into consideration. The parallelization efficiency mentioned here is equivalent to the amount of deterioration of the series resistor Rs when connecting the n negative resistance elements 101 for example, and ideal parallelization efficiency is when the combined resistance of the entire oscillation element is generally 1/n times as compared to when the number of the negative resistance elements 101 is one. However, there may be a case where this ideal parallelization efficiency is not satisfied depending on the positions of multiple negative resistance elements 101.

For example, let us assume that in a state in which, as illustrated in FIG. 1A, the two negative resistance elements 101 are electrically connected vertically surrounded with the strip conductors 103 and 104, the third new negative resistance element is added between the two negative resistance elements 101. With this way of positioning the three negative resistance elements, the series resistor Rs of the added negative resistance element is increased, and parallelization efficiency equivalent to deterioration in series resistance of the entire oscillation element is deteriorated.

In order to suppress deterioration in parallelization efficiency, with the present embodiment, protrusions 106 are provided to one end portion of the strip conductor 104 as illustrated in the drawing. Specifically, it is desirable to provide the protrusions 106 having a protruding shape formed so as to be positioned between the negative resistance elements, at an end portion positioned on the negative resistance element side of the strip conductor 104. As a reason thereof, the shortest distance between the strip conductor 104 and the three negative resistance elements 101 becomes equal, and accordingly, the series resistor Rs disposed in the middle is not increased, and deterioration in parallelization efficiency of the oscillation element may be suppressed. Note that the shapes of the protrusions are not restricted to a rectangle, and any shape may be employed.

In this manner, in the event that the number of the negative resistance elements 101 increases to three, four, . . . , n, it is effective to dispose the protrusions 106 of the strip conductor 104 made up of a material of which the electrical conductivity is higher than that of the conductor layer 102, between the negative resistance elements 101. Note that the protrusions 106 according to the present embodiment are important in an element array so that the phase difference between the negative resistance elements is sufficiently small. At this time, the protrusions may be disposed in a mesh manner.

Figure 5A:
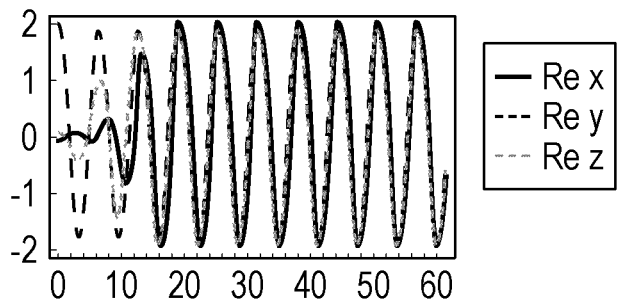
FIGS. 5A to 5C are diagrams illustrating time waveforms of terahertz waves of three negative resistance elements according to the second embodiment.
Figure 5B:
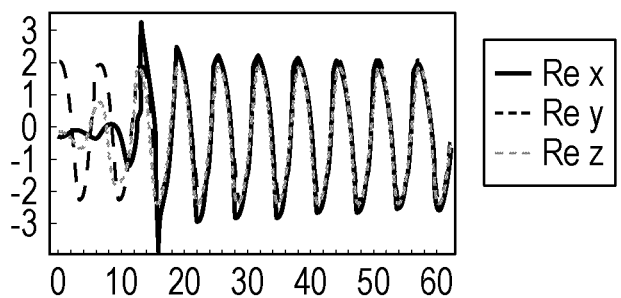
Figure 5C:
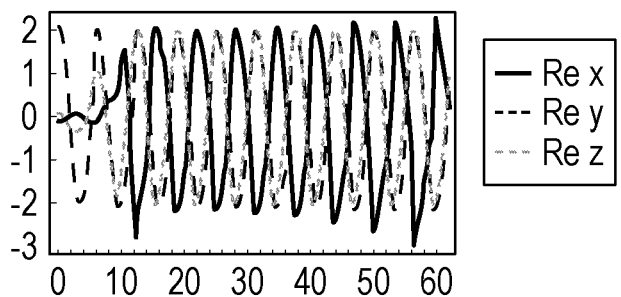

FIGS. 5A to 5C are diagrams for describing mutual injection locking of electromagnetic waves to be oscillated in the present embodiment. With the present embodiment, a case will be considered where injection locking is mutually performed between three negative resistance elements, and the simultaneous equations in FIGS. 3A to 3F will be extended, and expressions in the event that the three negative resistance elements are arrayed on an antenna will become as follows.

$$x''(\tau) - \lambda(1-x^2(\tau))x'(\tau) + x(\tau) = \lambda_{in} \varepsilon y'(\tau) \exp(i\phi_{xy}) + \lambda_{in} \varepsilon^2 z'(\tau) \exp(i(\phi_{xy}+\phi_{yz}))$$

$$y''(\tau) - \lambda(1-y^2(\tau))y'(\tau) + y(\tau) = \lambda_{in} \varepsilon (z'(\tau) \exp(i\phi_{yz}) + x'(\tau) \exp(i\phi_{xy}))$$

$$z''(\tau) - \lambda(1-z^2(\tau))z'(\tau) + z(\tau) = \lambda_{in} \varepsilon^2 x'(\tau) \exp(i(\phi_{xy}+\phi_{yz})) + \lambda_{in} \varepsilon y'(\tau) \exp(i\phi_{yz})$$

FIGS. 5A to 5C represent φ dependency that is phase difference between the negative resistance elements at the time of ∈=0.4, and illustrates computation results when setting $\phi=-\phi_{xy}=\phi_{yz}=\pi/16$, $\phi=-\phi_{xy}\phi_{yz}=\pi/8$, and $\phi=-\phi_{xy}=\phi_{yz}=\pi/4$, in order of FIGS. 5A, 5B, and 5C.

As illustrated in the drawings, when setting the phase difference φ of the three negative resistance elements as π/16 (FIG. 5A), or when setting the phase difference φ as π/8 (FIG. 5B), electromagnetic waves to be oscillated from the three negative resistance elements 101 are synchronized. In this manner, when considering a case where three, four, or generally n negative resistance elements 101 are disposed, in the event that the negative resistance elements 101 are disposed in a position in the common phase, i.e., a position where the phase differences of all of the negative resistance elements are between 0 and π/8, electromagnetic waves to be oscillated by all of the negative resistance elements are synchronized, and the oscillation frequencies and phases thereof become the common oscillation frequency and common phase. Therefore, oscillation output of the oscillation element may sufficiently be improved. Note that, with the oscillation element according to the present embodiment, in the event of the phase difference φ=π/4 (FIG. 5C), electromagnetic waves to be oscillated by the negative resistance elements have not been synchronized.

Also, with the present embodiment, an example has been described wherein the three negative resistance elements are apposed, but the present invention also encompasses a case where generally n negative resistance elements are disposed.

In the event that n negative resistance elements are disposed, oscillation output of the oscillation element increases n times. Accordingly, ten through one hundred 10-μW negative resistance elements are arrayed at around 1-THz oscillation frequency, and accordingly, oscillation output extent to around 10 μW though 1 mW may be realized.

Third Embodiment

While the positions of the multiple negative resistance elements have been described as a position to generate the common phase, electromagnetic waves may be synchronized even in a position to generate the opposite phase. With the present embodiment, description will be made regarding an embodiment wherein multiple negative resistance elements are disposed in a position to generate the opposite phase.

With the present embodiment as well, as with the case of the common phase, electromagnetic waves may sufficiently be synchronized as long as the phase difference is 7π/8 or greater and 9π/8 whereby the phase difference becomes π/8 from the position to generate the opposite phase.

Figure 6A:
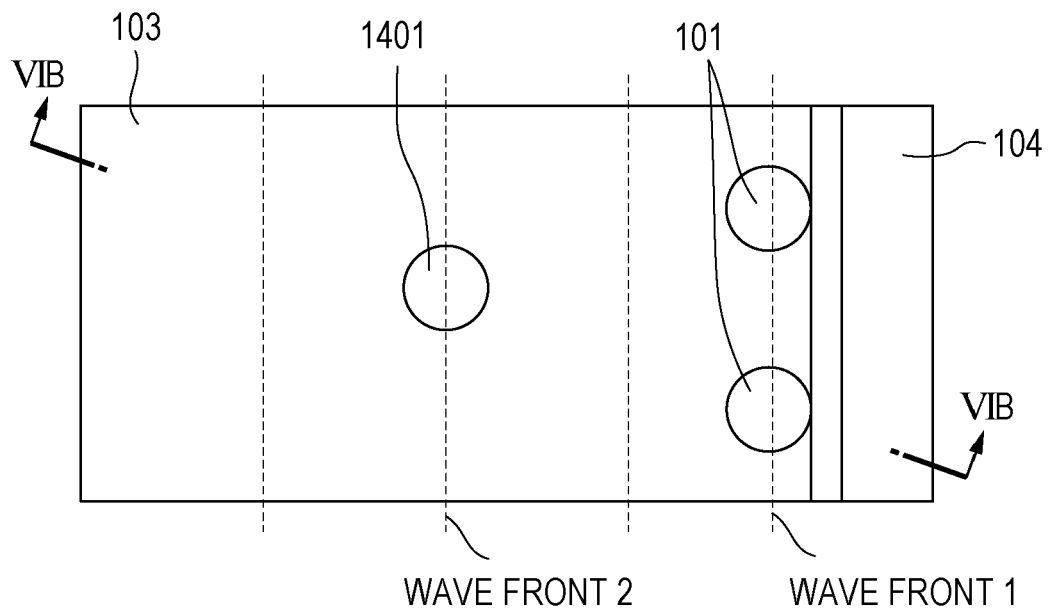
FIG. 6A is a schematic diagram illustrating a top face of an oscillation element according to a third embodiment.
Figure 6B:
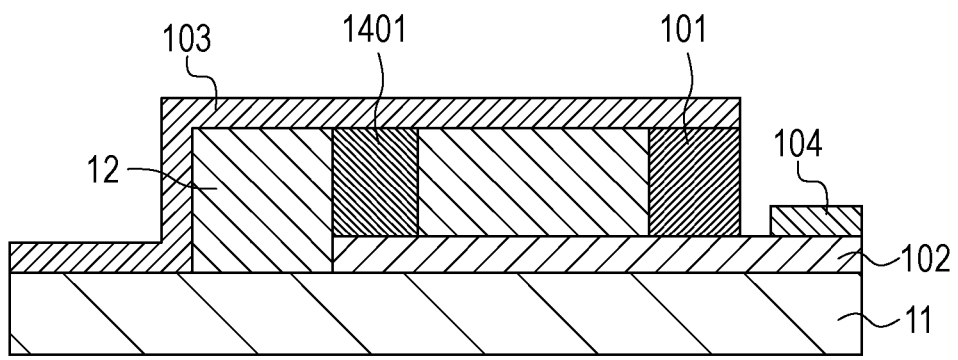
FIG. 6B is a schematic diagram illustrating a portion of a cross section of the oscillation element according to the third embodiment.

The oscillation element according to the present embodiment will be described with reference to FIGS. 6A and 6B. FIG. 6A is a top view illustrating a portion of the oscillation element according to the present embodiment. FIG. 6B is a cross-sectional view illustrating a portion of the oscillation element according to the present embodiment.

The present embodiment is equivalent to a modification of the first embodiment. With the first embodiment, the negative resistance elements (semiconductor elements) are disposed in a position of the common wave front, but with the third embodiment, a configuration example is illustrated wherein a negative resistance element (semiconductor element) 1401 is also disposed on a wave front of which the sign differs. With the present configuration example, a wave front 2 has a different sign from that of the wave front 1, and the others the same as with the first embodiment except that the shapes of the strip conductors partially differs.

Specifically, the multiple negative resistance elements are disposed in both of a position where the phases of electromagnetic waves which the negative resistance elements oscillate mutually are the same phase in a substantial manner, and a position where the phases mutually become the opposite phase.

With the present configuration example, in the event that the negative resistance element 1401 is interlocked with the negative resistance elements 101 at the opposite phase, oscillation output may increase three times.

Figure 7A:
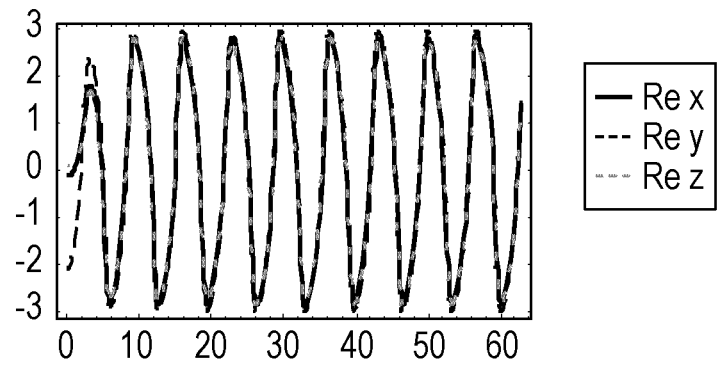
FIGS. 7A and 7B are diagrams illustrating time waveforms of terahertz waves of a negative resistance element according to the third embodiment.
Figure 7B:
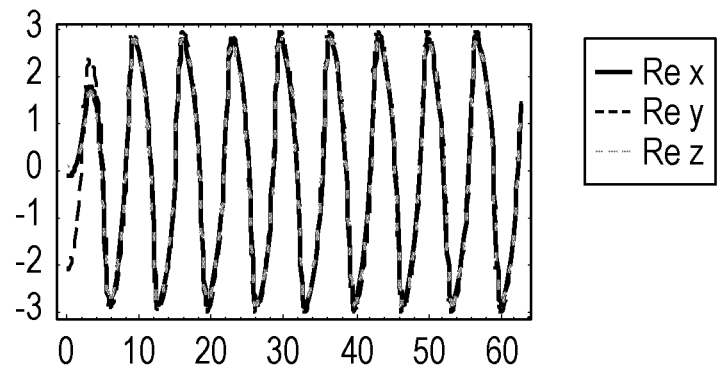

FIGS. 7A and 7B are a numeric computation example for describing mutual injection locking. With the present embodiment as well, numeric computation was performed based on the following expressions as with the second embodiment.

$$x''(\tau)-\lambda(1-x^2(\tau))x'(\tau)+x(\tau)=\lambda_{in}\in y'(\tau)\exp(i\phi_{xy})+\lambda_{in}\in^2 z'(\tau)\exp(i(\phi_{xy}+\phi_{yz}))$$

$$y''(\tau)-\lambda(1-y^2(\tau))y'(\tau)+y(\tau)=\lambda_{in}\in(z'(\tau)\exp(i\phi_{yz})+x'(\tau)\exp(i\phi_{xy}))$$

$$z''(\tau)-\lambda(1-z^2(\tau))z'(\tau)+z(\tau)=\lambda_{in}\in^2 x'(\tau)\exp(i(\phi_{xy}+\phi_{yz}))+\lambda_{in}\in y'(\tau)\exp(i\phi_{yz})$$

FIGS. 7A and 7B represent computation results at the time of ∈=0.4, FIG. 7A represents results when $\phi_{xy}=7\pi/8$, and $\phi_{yz}=9\pi/8$, and FIG. 7B represents results when $\phi_{xy}=9\pi/8$, and $\phi_{yz}=7\pi/8$.

With computation results, the sign for the element y alone is inversely displayed, but this is because, with the present embodiment, it is ideal that the element y is interlocked with the opposite phase of the elements x and z. When the n is ideal, and the element y is in a range of $7\pi/8 \le \phi 9\pi/8$, mutual injection locking is performed.

In the event that the number of the negative resistance elements 1041 increases such as two, and three, or even when generally considering multiple negative resistance elements 1041, the phase difference is in a position to generate the opposite phase sufficiently approximate to the π, cooperation is performed in the opposite phase. Further, a specific configuration of the oscillation element will be descried in detail in the following embodiments.

Fourth Embodiment

Configuration of Oscillator

Figure 8A:
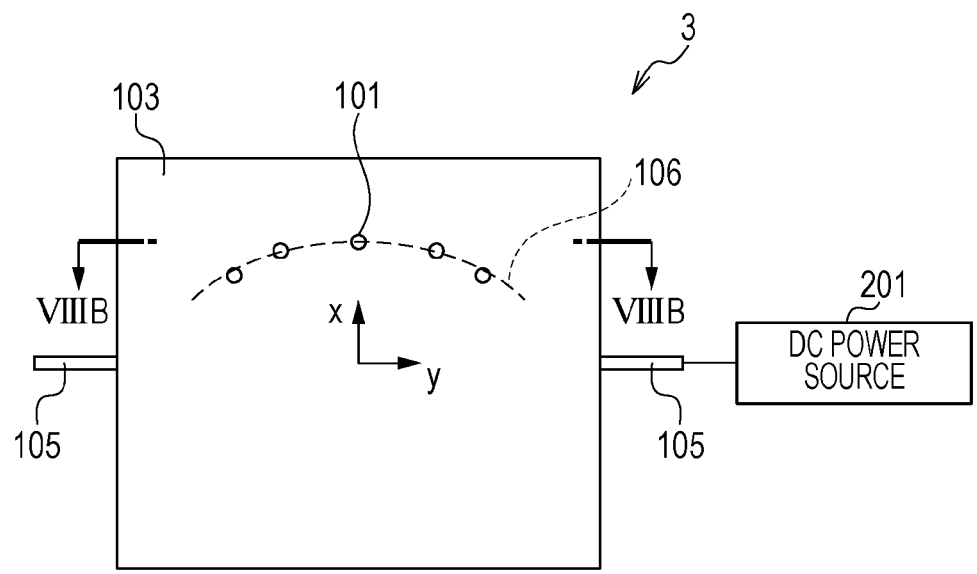
FIG. 8A is a diagram illustrating a schematic configuration of an oscillation element according to a fourth embodiment.
Figure 8B:
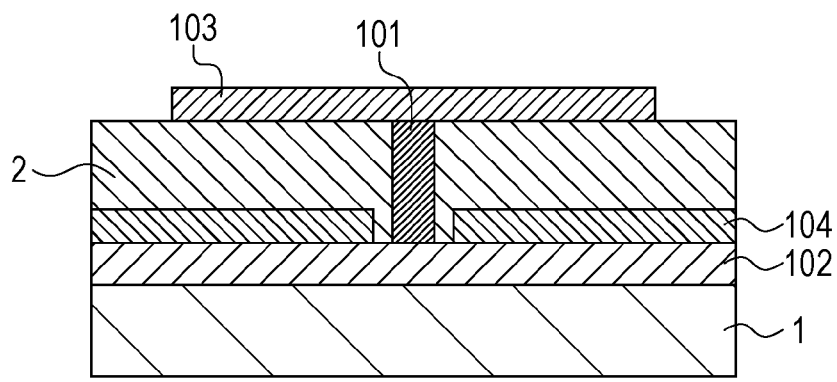
FIG. 8B is a diagram illustrating a cross section of the oscillation element according to the fourth embodiment.

An oscillation element and oscillator according to the present embodiment will be described. FIG. 8A is a schematic diagram illustrating the oscillator according to the present embodiment. FIG. 8B is a diagram illustrating the cross section of the oscillation element according to the present embodiment.

With the present embodiment, a resonant tunneling diode 101 which is a negative resistance element is a negative resistance element. With an oscillation element 3, a patch antenna 100 is employed as a planar antenna, and a resonant tunneling diode (hereinafter, also referred to as RTD) is disposed in the patch antenna 100.

The reason why the patch antenna has been employed is because the patch antenna is adapted to facilitate accumulation of a great number of RTDs, and to facilitate increase in oscillation output within a single antenna. The employed patch antenna 100 oscillates 0.5 THz, and with employed conductor patterns 103 and 104 which make up the patch antenna 100, one side is 150 μm, and the diameter of an RTD is 2 μm.

Supply of power to the oscillation element 3 is performed via high-impedance line 105 made up of a high-impedance member in the center portion of the conductor pattern 103 which is a patch antenna, and bias voltage is applied to the antenna 100 from a DC power source 201 which is a power supply unit which applies DC voltage to supply power to the antenna 100.

Thus, an electric field is formed in the resonant tunneling diode 101, and electromagnetic waves are oscillated from the oscillation element 3. Note that, with the oscillation element, occurrence of parasitic oscillation may be conceived, and accordingly, this may be shunted by inserting a low-impedance circuit. Also, as illustrated in the drawings, let us assume that the center of the patch antenna 100 is taken as the origin, and the surface of the antenna is taken as an x-y plane.

At this time, the positions of five resonant tunneling diodes 101 disposed so as to have the common phase for electromagnetic waves which the oscillation element oscillates were (x, y)=(30, −30 µm), (34, −20 µm), (42, 0 µm), (34, 20 µm), and (30, −30 µm).

Specifically, the multiple resonant tunneling diodes 101 were configured to be apposed in a gentle arc shape in the antenna. Here, the x direction is equivalent to the resonance direction of electromagnetic waves generated by the diodes. Accordingly, the arc may be linearly symmetrical across an axis parallel to the resonance direction of the electromagnetic waves.

Figure 9:
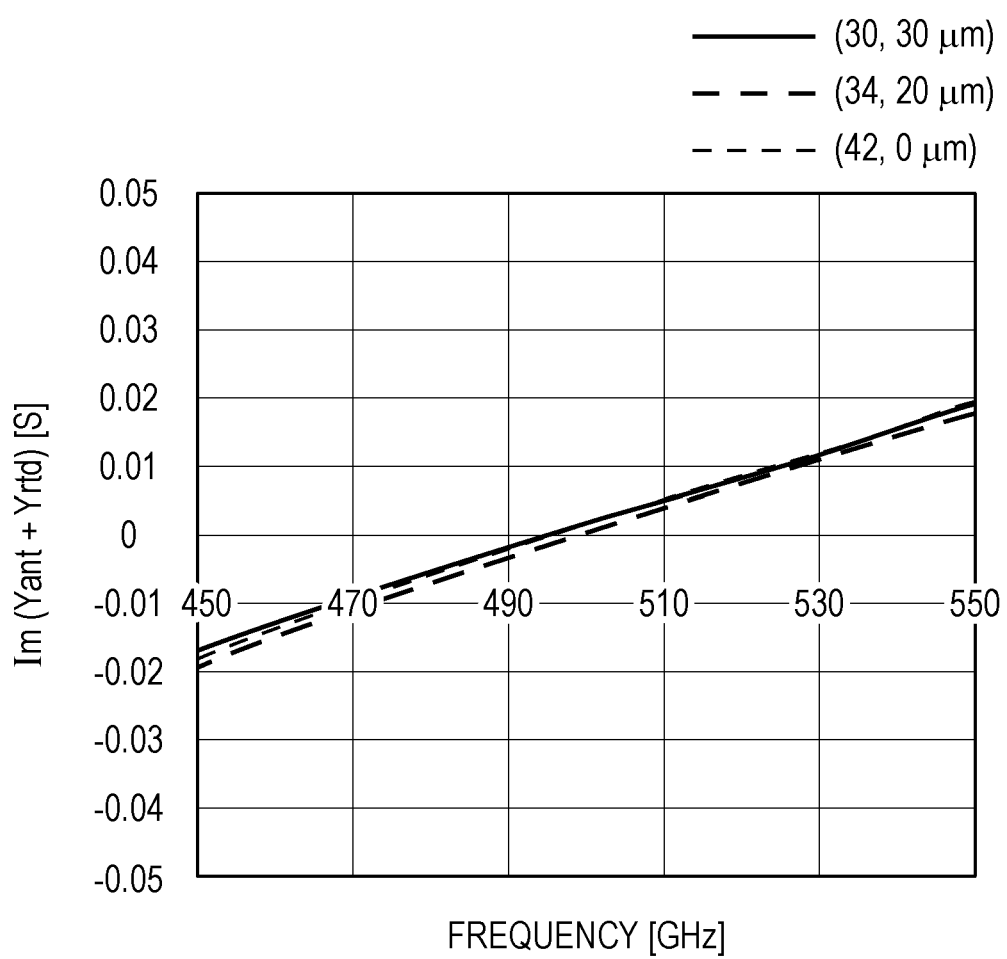
FIG. 9 is a diagram illustrating an imaginary component (susceptance) of admittance of the oscillation element according to the fourth embodiment.

FIG. 9 is a diagram illustrating computation results of admittance at the oscillation element according to the present embodiment. FIG. 9 illustrates results of admittance properties obtained by simulating the configuration of the oscillation element using a high-frequency total-field simulator HFSS v12 (manufactured by Ansoft)

Note that the data of (30, −30 µm) and (34, −20 µm) are equal to data in positions of (30, 30 µm) and (34, 20 µm) from geometric symmetry of the positions of the resonant tunneling diodes respectively, and accordingly will be omitted.

The admittance properties include reactance of the resonant tunneling diodes 101 which are negative resistance elements, and an gentle arc wave front in a protruding shape toward the outside from the center of the patch antenna 100 become a plane of the common phase of electromagnetic waves at a patch-antenna-type resonator 4.

With the present embodiment, in order that the susceptance illustrated in the vertical axis in FIG. 9 becomes equal to zero, the frequency of electromagnetic waves which the oscillation element oscillates was designed to be between 490 GHz and 500 GHz, i.e., within 2%. In FIGS. 8A and 8B, the array of the five resonant tunneling diodes 101 is slightly shifted from the plane of the common phase, but this range may be said to be a range which enables the electromagnetic waves which the five resonant tunneling diodes 101 oscillate to be synchronized.

Manufacturing Method of Oscillation Element

The oscillation element according to the present embodiment was manufactured by the following method. First, multiple layers were subjected to epitaxial growth on an InP substrate 1 using the molecular beam epitaxy (MBE) method or metal organic vapor phase epitaxy (MOVPE) method or the like.

Specifically, layers of n-InP/n-InGaAs, and InGaAS/In-AlAs were subjected to epitaxial growth in order. Thereafter, n-InGaAs was subjected to epitaxial growth to employ an N-type electro-conductive substrate as the InP substrate. Also, at the that time, the processes such as familiar etching, cleansing, impurity implantation, exposure, and so forth were performed to form a resonant tunneling diode layer and an electrical contact layer.

Further, the resonant tunneling diode layer and electrical contact layer were subjected to etching so as to have a cylindrical mesa shape. Further, the resonant tunneling diode layer 101 and electrical contact layer 102 were subjected to etching so as to have an arc mesa shape of which the cross-sectional area is 2 µm². As for etching, dry etching according to EB (Electron Beam) lithography and ICP (Inductively-coupled plasma) was employed, but photolithography may be employed instead.

Next, grounding metal made up of aluminum was formed on the surface of the electrical contact layer by the liftoff method. Here, passivation has to be formed for protecting a side wall at the resonant tunneling diode layer 101.

BCB32 is formed with film thickness of around 3 µm was formed on a portion serving as a resonator so as to expose n-InP/n-InGaAs 302 using the spin coat method and dry etching. The oscillation element is completed by lastly forming Ti/Pd/Au using the liftoff method.

Modifications of Antenna

Figure 12A:
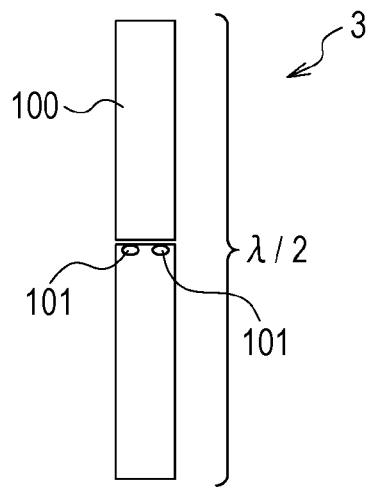
FIGS. 12A to 12C are diagrams illustrating a modification of the oscillation element according to the fourth embodiment.
Figure 12B:
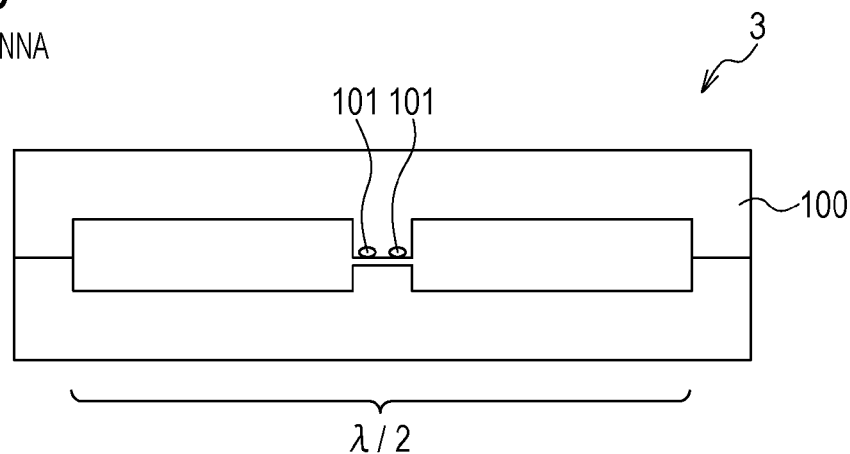
Figure 12C:
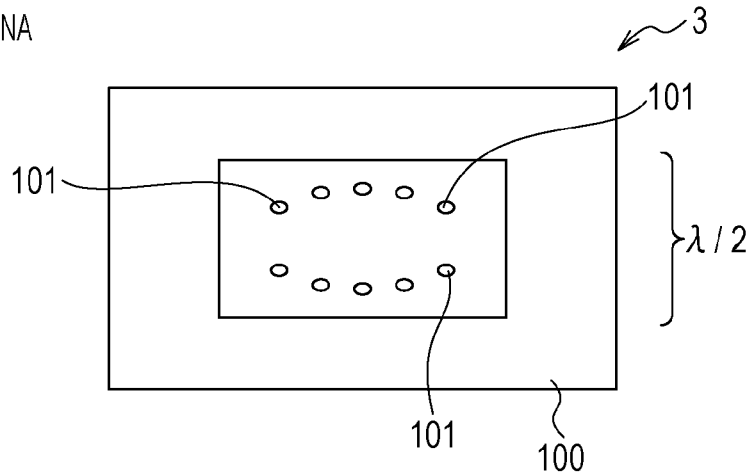

FIGS. 12A to 12C are diagrams illustrating a modification of an antenna to which the present embodiment may be applied. A dipole antenna and a slot antenna illustrated in FIGS. 12A and 12B may be employed. Also, a negative resistance element with the common phase and a negative resistance element with the opposite phase may be synchronized, as illustrated in FIG. 12C, by employing a patch antenna, and disposing a negative resistance element in the opposite phase which differs from the original phase by π. Also, the multiple negative resistance elements may be disposed in a position where the sign in the electric field at a patch antenna resonator is reversed. Specifically, at the time of disposing the multiple negative resistance elements, the negative resistance elements have to be disposed in a position to generate the common phase or opposite phase of electromagnetic waves.

Also, the antenna 100 is not restricted to a planar antenna, and may be a portion equivalent to the primary radiator of a stereo antenna or Cassegrain antenna or parabolic antenna.

Also, it is desirable that a conductor pattern which is in contact with the resonant tunneling diode 101 is flat so as to readily define the phases and wave fronts (e.g., equipotential surfaces of electromagnetic waves) of electromagnetic waves at the conductor patterns 103 and 104.

Also, the present invention is not restricted to the oscillation element being configured with the same negative resistance elements, and negative resistance elements having a different type or different dimensions may be employed.

Fifth Embodiment

An oscillation element according to the present embodiment is characterized to include multiple resonant tunneling diodes with a different junction area and different reactance. The oscillation element according to the present embodiment will be described below. However, description will be omitted regarding the same configurations as with the fourth embodiment.

Figure 10A:
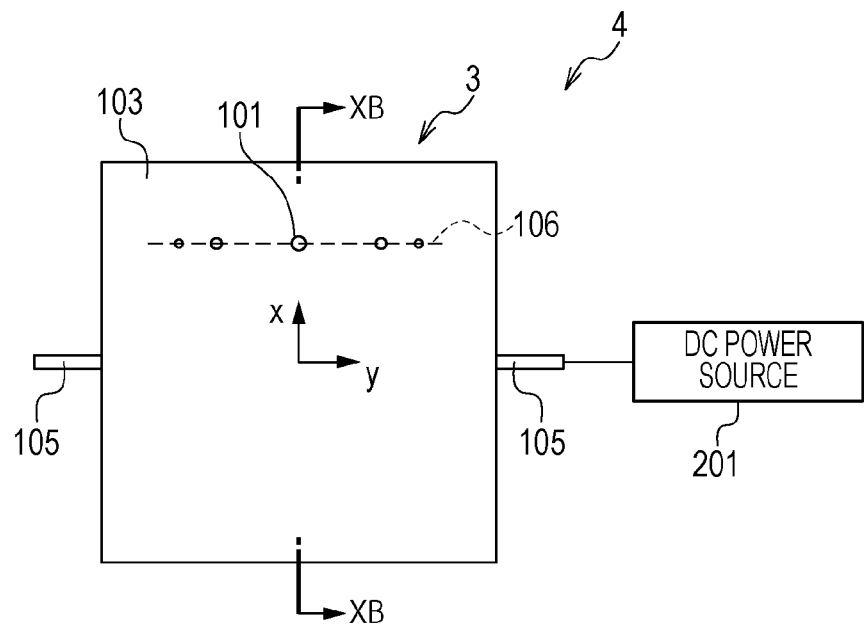
FIG. 10A is a diagram illustrating a schematic configuration of an oscillator according to a fifth embodiment.
Figure 10B:
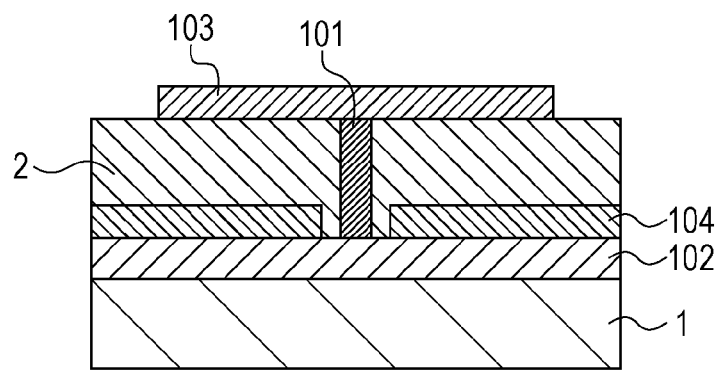
FIG. 10B is a diagram illustrating a cross section of the oscillator according to the fifth embodiment.

FIGS. 10A and 10B are diagrams illustrating the oscillation element according to the present embodiment. With the present embodiment as well, resonant tunneling diodes will be employed as negative resistance elements.

FIG. 10A is a schematic diagram of an oscillator including resonant tunneling diodes, and FIG. 10B is a cross-sectional view of the oscillator including resonant tunneling diodes.

With the present embodiment, multiple resonant tunneling diodes having a different junction area are integrated in a conductor pattern. A patch antenna 100 including conductor patterns 103 and 104 is an antenna to oscillate around 0.5 THz, and one side of each of the conductor patterns 103 and 104 is 150 µm.

With the oscillation element according to the present embodiment, when assuming an x-y plane with the center of the patch antenna 103 as the origin, the positions of five resonant tunneling diodes 101 are (x, y)=(40, −40 µm), (40, −30 µm), (40, 0 µm), (40, 30 µm), and (40, 40 µm).

With the present embodiment, the resonant tunneling diodes 101 having a different area are disposed in the corresponding points, and the diameters of the resonant tunneling diodes are, in order from smaller x, 1.8 m, 1.9 µm, 2.0 µm, 1.9 µm, and 1.8 µm. Also, the shape of any of the resonant tunneling diodes is a cylinder.

Figure 11:
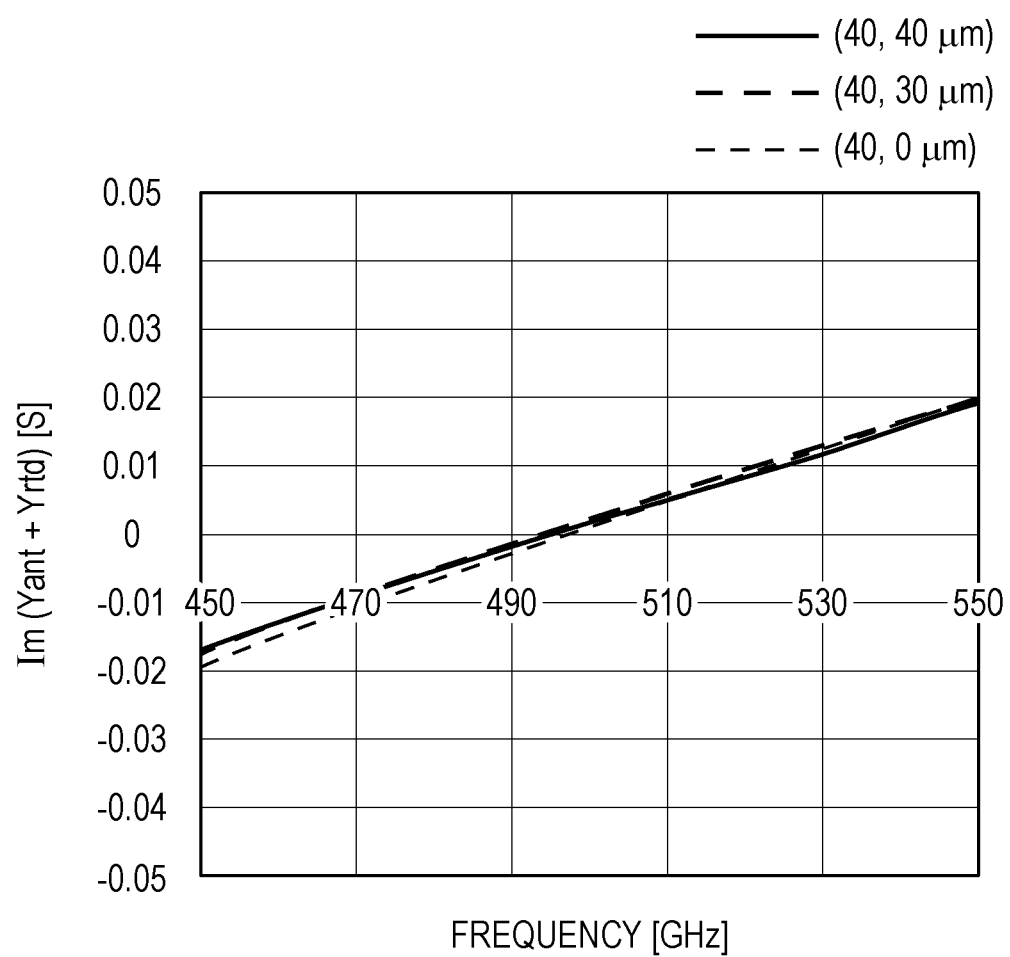
FIG. 11 is a diagram illustrating an imaginary component (susceptance) of admittance of the oscillator according to the fifth embodiment.

FIG. 11 illustrates computation results of admittance properties at the oscillation element according to the present embodiment. Simulation was performed with the same conditions as with FIG. 9.

The multiple resonant tunneling diodes are disposed so that the junction areas of the resonant tunneling diodes become small toward the outside from the center of the patch antenna 100. In the event of disposing such resonant tunneling diodes 101 with a different junction area, a linear-shaped wave front 106 illustrated in the drawing becomes the common phase of phase difference φ of electromagnetic waves within the patch-antenna-type resonator. Therefore, with the oscillator according to the present embodiment, the resonant tunneling diodes 101 are linearly disposed in the antenna.

The present embodiment was designed so that the frequency bands of electromagnetic waves which the five resonant tunneling diodes 101 oscillate are between 490 GHz to 500 GHz, within 2%.

It may be understood that the plane of the common phase of the phase difference φ at electromagnetic waves to be resonated at the antenna 100 depends on reactance of the resonant tunneling diodes 101. Accordingly, after taking the reactance of the resonant tunneling diodes 101 into consideration as well, the resonant tunneling diodes 101 are disposed on the common phase surface of electromagnetic waves having the desired oscillation frequency or the opposite phase surface where the phase difference becomes π, whereby electromagnetic waves which the multiple resonant tunneling diodes 101 oscillate may be synchronized and the frequency and phase thereof may be aligned.

Sixth Embodiment

An oscillation element according to the present embodiment is characterized to be disposed in a stereo antenna by being connected to a waveguide. The oscillation element according to the present embodiment will be described below. However, description will be omitted regarding the same configurations as with the fourth embodiment.

Figure 13A:
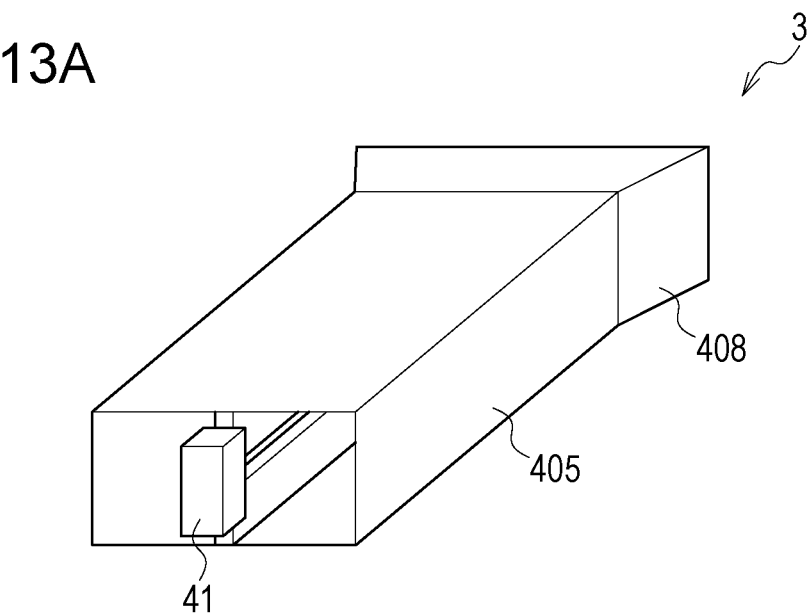
FIG. 13A is a diagram illustrating a schematic configuration of an oscillation element according to a sixth embodiment.
Figure 13B:
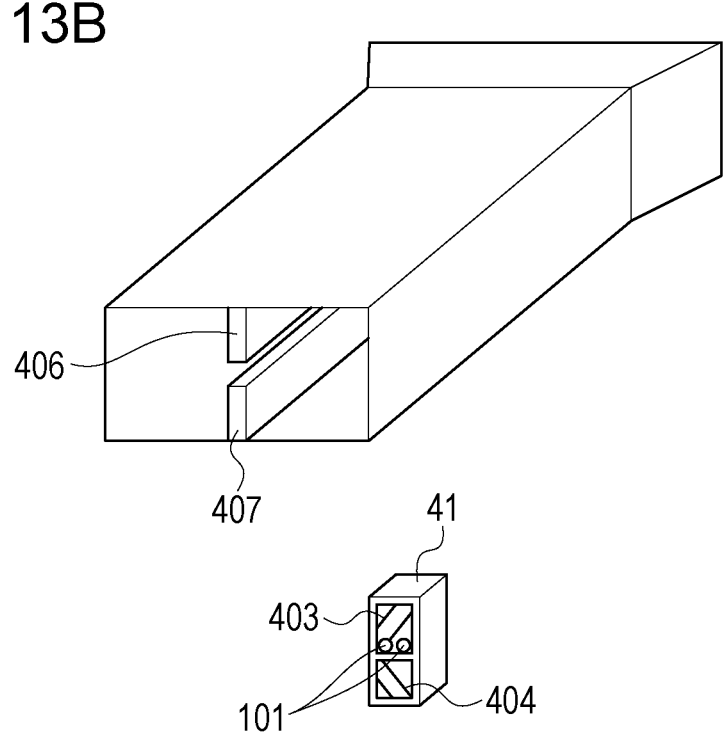
FIG. 13B is a diagram illustrating a schematic configuration as a semiconductor chip of the oscillation element according to the sixth embodiment has been removed.

FIG. 13A is a perspective view illustrating the oscillation element according to the present embodiment. FIG. 13B is a perspective view of a semiconductor chip including an Esaki diode and the oscillator from which the semiconductor chip has been removed. With the present embodiment, Esaki diodes are employed as negative resistance elements.

In the drawings, the configuration of a traveling-wave antenna for electromagnetic waves and a waveguide. With the present embodiment, a double ridge waveguide serving as a horn antenna and a resonator is included, and also, a semiconductor chip 41 including an Esaki diode is assembled therein. The present embodiment is an example wherein a waveguide which is electrically connected to the antenna and transmits electromagnetic waves is provided, and multiple negative resistance elements are connected to the waveguide.

The horn antenna has features to excel in wideband properties and to have sharp directivity. In order to guide and resonate electromagnetic waves from the semiconductor chip, a double ridge waveguide 405 is employed.

The traveling-wave antenna oscillates 300 GHz to 0.1 THz, and accordingly, a horn antenna 408 includes an opening of 3.5 mm×7.0 mm on the narrowest near side of the drawing with one side having dimensions of four times thereof on the widest far side.

The length of the double ridge waveguide 405 is taken as around a few millimeters with length corresponding to this frequency band. Ridges 406 and 407 in the double ridge waveguide 405 extend from the vertical direction in the drawing, and the semiconductor chip is mounted by soldering or the like.

With a configuration of the semiconductor chip 41 according to the present embodiment, a p-n junction is formed with a p-type layer/n-type layer according to GaAs on a GaAs substrate, and two mesa-type Esaki diodes 101 having a 5-µm diameter are provided. In reality, ohmic electrodes 403 and 404 which are two electrodes of an Esaki diode are electrically connected to the ridges 406 and 407.

With the Esaki diode of an end portion of the double ridge waveguide 405, electromagnetic waves reflected from a discontinuous point between the double ridge waveguide 405 and the antenna 408 are standing. Therefore, the two mesa-type Esaki diodes 101 within the semiconductor chip may be disposed in a position to generate the common phase of electromagnetic waves to be oscillated. That is to say, the multiple Esaki diodes 101 are disposed so as to be the common phase (or opposite phase) for electromagnetic waves to be oscillated from the antenna via the double ridge waveguide 405.

Figure 14:
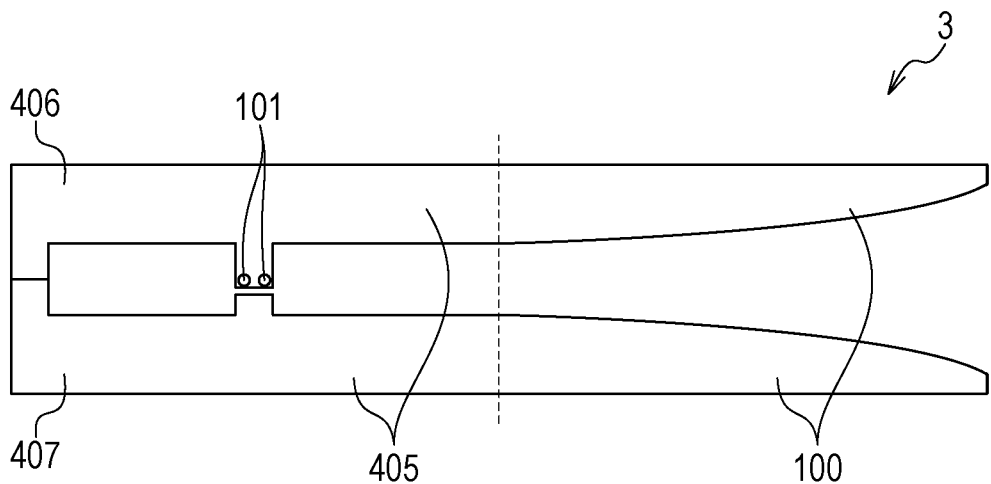
FIG. 14 is a diagram illustrating a configuration in which the oscillation element according to the sixth embodiment has been applied to a planar antenna.

FIG. 14 is a diagram illustrating a configuration wherein the oscillation element has been applied to a planar antenna. The oscillation element 3 includes a tapered slot antenna 100, and a slot line 405 (406, 407) as a transmission line, and is configured wherein the two resonant tunneling diodes 101 are disposed in the slot line 406.

Other Embodiments

Figure 15:
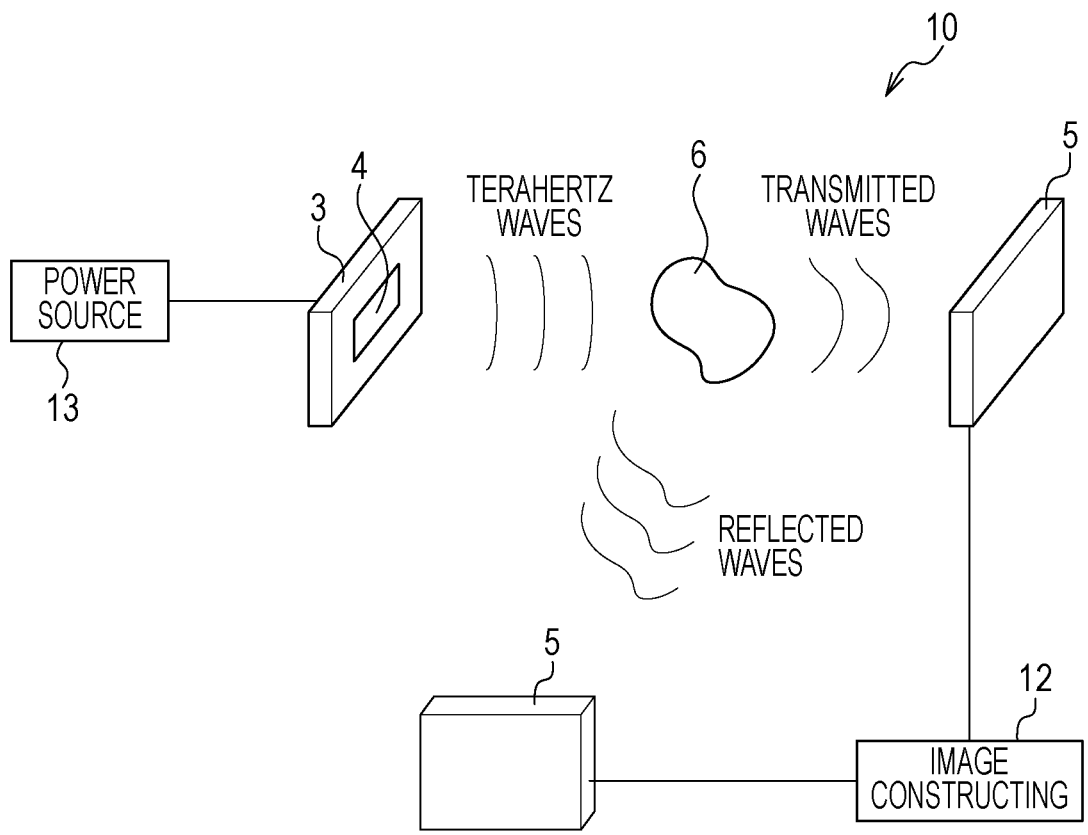
FIG. 15 is a diagram illustrating a configuration of an imaging apparatus according to another embodiment.

Another preset embodiment is an imaging apparatus employing the oscillation element described so far FIG. 15 is a schematic diagram illustrating the imaging apparatus according to the present embodiment. An imaging apparatus 10 according to the present embodiment images an object to be measured using electromagnetic waves. Also, electromagnetic waves to be employed are electromagnetic waves with a frequency band of 0.5 THz which have relatively transparency to image an object to be measured using the electromagnetic wave properties of terahertz waves.

The present embodiment is characterized by an imaging apparatus 10 including an oscillator 4 including the oscillation element described in the embodiments so far, two detectors 5 configured to receive terahertz waves, an image constructing unit 12 configured to construct an image of an object to be measured based on information relating to electromagnetic waves which transmit or reflect the object to be measured which multiple detecting elements each detect.

Terahertz waves are radiated on an object to be measured 6 from the antenna of the oscillation element 3 described so far, and then, transmitted waves which transmitted the object to be measured of the terahertz waves are detected by the detector 5. Also, terahertz waves reflected and scattered from the object to be measured are also detected by the detector 5.

At this time, physical property information such as absorption spectrum or refractive index of the object to be measured or the like is obtained from a signal relating to electric field strength of terahertz waves detected by the detecting element 3. Also, the physical property information of the object to be measured may be visualized by constructing an image of the object to be measured from this obtained physical property information.

The transmitted waves of the terahertz waves are effective for perspective such as security, process inspection of an object having specific absorption, and so forth. Also, scattering of the terahertz waves is effective for an imaging apparatus which images an object to be measured with the same principles as with a camera or the like, and so forth. Accordingly, in the event of employing multiple detectors including a detecting element, there may be configured an imaging apparatus 10 including an image constructing unit 12 which constructs an image from information relating to physical properties of an object to be measured 6 based on information relating to electromagnetic waves detected by each of the detecting elements.

At this time, this imaging apparatus 10 may also be upgraded to an imaging apparatus which handles different frequency bands by disposing an oscillation element 3 having different antenna lengths. Also, this imaging apparatus 10 may also be upgraded to an imaging apparatus which handles different polarized waves of electromagnetic waves by disposing an oscillation element 3 having different antenna directions.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-009336 filed Jan. 19, 2012 and No. 2013-006315 filed Jan. 17, 2013, which are hereby incorporated by reference herein in their entirety.

What is claimed is:

1. An oscillation element configured to oscillate electromagnetic waves, comprising:
    an antenna configured to guide electromagnetic waves; and
    a plurality of negative resistance elements electrically serially connected to the antenna, and also connected to each other electrically in parallel;
    wherein the plurality of negative resistance elements are configured to oscillate a plurality of electromagnetic waves, and are disposed in positions relative to one another such that the absolute values of phase differences of the electromagnetic waves which the corresponding negative resistance elements oscillate, are 0 or greater and $\pi/8$ or less, or are $7\pi/8$ or greater and $9\pi/8$ or less, and
    wherein the positions are positions where oscillation frequencies of the electromagnetic waves which the corresponding negative resistance elements oscillate are equal.

2. The oscillation element according to claim 1, wherein at least one conductor which makes up the antenna is electrically serially connected to the negative resistance elements via a semiconductor layer.

3. The oscillation element according to claim 1, wherein the antenna is made up of a pair of conductors, and the plurality of negative resistance elements are apposed in contact with one conductor of this pair.

4. The oscillation element according to claim 1, wherein the plurality of negative resistance elements are disposed in an arc shape.

5. The oscillation element according to claim 4, wherein the arc makes up line symmetry with an axis parallel to the resonance direction of the electromagnetic waves as a boundary.

6. The oscillation element according to claim 1, wherein the plurality of negative resistance elements are mutually equal in the area of a cross section perpendicular to a direction where current of a junction portion making up the corresponding negative resistance element flows.

7. The oscillation element according to claim 1, wherein the plurality of negative resistance elements are linearly disposed.

8. The oscillation element according to claim 7, wherein the plurality of negative resistance elements mutually differ in the area of a cross section perpendicular to a direction where current of a junction portion making up the corresponding negative resistance element flows.

9. The oscillation element according to claim 1, wherein electromagnetic waves including a part of frequency bands of 30 GHz to 30 THz are able to be oscillated.

10. The oscillation element according to claim 1, wherein the plurality of negative resistance elements are disposed in positions relative to one another such that the absolute values of phase differences of the electromagnetic waves which the corresponding negative resistance elements oscillate, are 0 or greater and $\pi/16$ or less, or are $7\pi/8$ or greater and $9\pi/8$ or less.

11. The oscillation element according to claim 1, wherein the antenna is a patch antenna.

12. The oscillation element according to claim 1, wherein each of the plurality of negative resistance elements has a cross section perpendicular to a direction where the current of a junction portion which makes up this negative resistance element flows, of which the area is 10 $\mu m^2$ or less.

13. The oscillation element according to claim 1, wherein the plurality of negative resistance elements are configured of silicon; and
    wherein each of the plurality of negative resistance elements has a cross section perpendicular to a direction where the current of a junction portion which makes up this negative resistance element flows, of which the area is 1 $\mu m^2$ or less.

14. The oscillation element according to claim 1, wherein the plurality of negative resistance elements are configured of a compound semiconductor material.

15. The oscillation element according to claim 14, wherein the plurality of negative resistance elements are configured of a Group III-V semiconductor material.

16. The oscillation element according to claim 1, wherein the plurality of negative resistance elements are resonant tunneling diodes.

17. The oscillation element according to claim 1, further comprising:
    a waveguide which is electrically connected to the antenna to transmit electromagnetic waves;
    wherein the plurality of negative resistance elements are connected to the waveguide.

18. The oscillation element according to claim 1, wherein the antenna has a protrusion, and is disposed so that the protrusion is positioned between the plurality of negative resistance elements.

19. An imaging apparatus configured to image an object to be measured using electromagnetic waves, comprising:
    an oscillator configured to oscillate electromagnetic waves to an object to be measured; and a detector configured to detect electromagnetic waves transmitted through or reflected at the object to be measured;

wherein the oscillator comprises the oscillation element according to claim 1.

20. An oscillation element configured to oscillate electromagnetic waves, comprising:

an antenna configured to guide electromagnetic waves; and a plurality of negative resistance elements electrically serially connected to the antenna, and also connected to each other electrically in parallel;

wherein the plurality of negative resistance elements include a first negative resistance element, a second negative resistance element and a third negative resistance element, and wherein the first negative resistance element is disposed in a position where the phase of an electromagnetic wave which the first negative resistance elements oscillates is the same as the phase of an electromagnetic wave which the third negative resistance element oscillates in a substantial manner, and the second negative resistance element is disposed in a position where the phase of an electromagnetic wave which the second negative resistance elements oscillates is opposite to the phase of the electromagnetic wave that the third negative resistance element oscillates in a substantial manner.

21. The oscillation element according to claim 20, wherein the first negative resistance element is disposed in a position where the absolute values of phase differences between the electromagnetic wave which the first negative resistance element oscillates and the electromagnetic wave which the third negative resistance element oscillates are 0 or greater and $\pi/8$ or less, and wherein the second negative resistance element is disposed in a position where the absolute values of phase differences between the electromagnetic waves which the second negative resistance elements oscillates and the electromagnetic wave which the third negative resistance element oscillates are $7\pi/8$ or greater and $9\pi/8$ or less.

22. The oscillation element according to claim 1, wherein the plurality of negative resistance elements are disposed in positions relative to one another such that the phase of each of the electromagnetic waves which the corresponding negative resistance elements oscillate, is the same phase in a substantial manner or is the opposite phase in a substantial manner to phases of other of the plurality of electromagnetic waves.

23. An imaging apparatus configured to image an object to be measured using electromagnetic waves, comprising:

an oscillator configured to oscillate electromagnetic waves to an object to be measured; and a detector configured to detect electromagnetic waves transmitted through or reflected at the object to be measured;

wherein the oscillator comprises the oscillation element according to claim 20.

24. An oscillation element configured to oscillate electromagnetic waves, comprising:

an antenna configured to guide electromagnetic waves; and a plurality of negative resistance elements electrically serially connected to the antenna, and also connected to each other electrically in parallel;

wherein the plurality of negative resistance elements are configured to oscillate a plurality of electromagnetic waves, and are disposed in positions relative to one another such that the phases of each of the electromagnetic waves which the corresponding negative resistance elements oscillate, is the same phase in a substantial manner or is the opposite phase in a substantial manner to phases of other of the plurality of electromagnetic waves;

wherein the positions are positions where oscillation frequencies of the electromagnetic waves which the corresponding negative resistance elements oscillate are equal, and wherein the plurality of negative resistance elements are disposed in an arc shape.

25. An oscillation element configured to oscillate electromagnetic waves, comprising:

an antenna configured to guide electromagnetic waves; and a plurality of negative resistance elements electrically serially connected to the antenna, and also connected to each other electrically in parallel;

wherein the plurality of negative resistance elements are configured to oscillate a plurality of electromagnetic waves, and are disposed in positions relative to one another such that the phases of each of the electromagnetic waves which the corresponding negative resistance elements oscillate, is the same phase in a substantial manner or is the opposite phase in a substantial manner to phases of other of the plurality of electromagnetic waves;

wherein the positions are positions where oscillation frequencies of the electromagnetic waves which the corresponding negative resistance elements oscillate are equal;

wherein the plurality of negative resistance elements are linearly disposed, and wherein the plurality of negative resistance elements mutually differ in the area of a cross section perpendicular to a direction where current of a junction portion making up the corresponding negative resistance element flows.

* * * * *